(12) United States Patent
Chiaradia

(10) Patent No.: US 9,969,862 B2
(45) Date of Patent: May 15, 2018

(54) PLASTICIZERS FOR POLYMERS

(71) Applicant: FLUOS S.A.S. DI GIUSEPPE CHIARADIA & C., Turin (IT)

(72) Inventor: Giuseppe Chiaradia, Turin (IT)

(73) Assignee: FLUOS S.A.S. DI GIUSEPPE CHIARADIA & C., Turin (IT)

( * ) Notice: Subject to any disclaimer, the term of this patent is extended or adjusted under 35 U.S.C. 154(b) by 32 days.

(21) Appl. No.: 15/033,916

(22) PCT Filed: Nov. 10, 2014

(86) PCT No.: PCT/EP2014/074208
§ 371 (c)(1),
(2) Date: May 3, 2016

(87) PCT Pub. No.: WO2015/067814
PCT Pub. Date: May 14, 2015

(65) Prior Publication Data
US 2016/0264758 A1    Sep. 15, 2016

(30) Foreign Application Priority Data
Nov. 11, 2013  (IT) .............. PN2013A0066

(51) Int. Cl.
C07D 303/40 (2006.01)
C07D 407/12 (2006.01)
C08K 5/00 (2006.01)
C08K 5/10 (2006.01)
C08K 5/1515 (2006.01)
C08K 5/1565 (2006.01)

(52) U.S. Cl.
CPC .......... *C08K 5/1515* (2013.01); *C07D 303/40* (2013.01); *C07D 407/12* (2013.01); *C08K 5/0016* (2013.01); *C08K 5/10* (2013.01); *C08K 5/1565* (2013.01)

(58) Field of Classification Search
CPC .. C07D 303/40; C07D 407/12; C08K 5/0016; C08K 5/10; C08K 5/1515; C08K 5/1565
USPC ........................................ 524/114
See application file for complete search history.

(56) References Cited

U.S. PATENT DOCUMENTS

2012/0021962 A1    1/2012   Selifonov

FOREIGN PATENT DOCUMENTS

| CN | 101346067 A | 1/2009 | |
|---|---|---|---|
| JP | H1095748 | 4/1998 | |
| RO | 128511 | 6/2013 | |
| WO | 2009010527 A1 | 1/2009 | |
| WO | 2010036884 A1 | 4/2010 | |
| WO | WO-2010036884 A1 * | 4/2010 | ........... C07D 317/30 |
| WO | 2012018939 A2 | 2/2012 | |
| WO | WO-2012018939 A2 * | 2/2012 | ........... C07D 317/30 |

OTHER PUBLICATIONS

International Search Report and Written Opinion of PCT/EP2014/074208 dated Jun. 22, 2015.

* cited by examiner

*Primary Examiner* — Ling Siu Choi
*Assistant Examiner* — Ronald Grinsted
(74) *Attorney, Agent, or Firm* — Silvia Salvadori, P.C.; Silvia Salvadori

(57) ABSTRACT

The present invention refers to plasticizers derived from vegetable oils for thermoplastic polymers and resins, in particular, plasticizers for Polyvinylchloride (PVC). Furthermore, the invention relates to a method for preparing such plasticizers. Plasticizers comprise esters of carboxyl fatty acids wherein fatty acids are selected from those having a hydrocarbon chain comprised between $C_{12}$ e $C_{22}$, wherein the double bonds of the hydrocarbon chain of the carboxylic fatty acid are epoxidized, and the esterification is with a cyclic acetal or ketal.

7 Claims, 1 Drawing Sheet

| FATTY ACID COMPOSITION (PERCENTAGE) | | | | | | | | | | |
|---|---|---|---|---|---|---|---|---|---|---|
| No. | Name of the Oil | Myristic (Tetradecanoic) C14 | Palmitic (Hexadecanoic) C16 | Stearic (n-Octadecanoic) C18 | Oleic (C18:1) | Linolenic (C18:3) | Linoleic (C18:2) | Arachidic C20 (Eicosanoic) | C20:1 | C22:1 | Any special fatty acid |
| 1 | Canola | ----- | 4.1 | 1.5 | 63.0 | 8.6 | 20.0 | | 1.9 | 41.0 | |
| 2 | Linseed Oil (Flax Seed Oil) | ----- | 4.0-7.0 | 2.0-5.0 | 12.0-34.0 | 35.0-60.0 | 17.0-24.0 | 0.3-1.0 | ----- | ----- | ----- |
| 3 | Palm Oil | 0.5-2.0 | 32.0-45.0 | 2.0-7.0 | 38.0-52.0 | ----- | 5.0-11.0 | ----- | ----- | ----- | ----- |
| 4 | Rapeseed | ----- | 4.0 | 1.5 | 17.0 | 9.0 | 13.0 | ----- | 14.5 | 41.0 | ----- |
| 5 | Soya Bean Oil | ----- | 7.0-12.0 | 2.0-5.0 | 19.0-30.0 | 7.0-10.0 | 48.0-52.0 | ----- | ----- | ----- | ----- |
| 6 | Sunflower Seed Oil | ----- | 3.0-6.0 | 1.0-3.0 | 14.0-35.0 | ----- | 44.0-75.0 | 0.6-4.0 | ----- | ----- | Behenic 0.8 |

PLASTICIZERS FOR POLYMERS

This application is a U.S. national stage of PCT/EP2014/074208 filed on 10 Nov. 2014 which claims priority to and the benefit of Italian Application No. PN2013A000066 filed on 11 Nov. 2013, the content of which are incorporated herein by reference in its entirety.

FIELD OF THE INVENTION

The present invention relates to plasticizers derived from vegetable oils for thermoplastic polymers and resins, in particular, plasticizers for Polyvinylchloride (PVC). Furthermore, the invention relates to a method for preparing such plasticizers.

BACKGROUND OF THE INVENTION

PVC resin could be used in the rigid form, not plasticized, for producing in general pipes, connections, profilates. For increasing flexibility of the polymer, in order to extend application opportunities, it is necessary to blend it with substances named plasticizers; in this manner the polymer can be used to make various products: films, toys, electrical cables, flexible pipes, flooring, etc.

Generally, plasticizers are liquids of high molecular weight, with solvency properties for polymeric products. In order to have a good plasticization, plasticizers must be mixed with the polymer at warm temperature. In this manner it can be absorbed into the amorphous network of the polymer.

In particular, the repeated monomeric unit of PVC is the following:

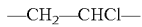

The presence of Chlorine, with high electronegativity, into the structure of the monomer gives polarity to the polymer. The long chains —$CH_2$—$CHCl$— are weakly bonded through dipole-dipole bonds between carbon atoms directly bonded to chlorine atoms, with low electronic density, and chlorine atoms of another chain. These secondary bonds, less strong respect to primary covalent bonds, make the product rigid and with poor resistance to flexibility.

Conversely, plasticizers molecules are composed of a polar side, represented normally by carboxylic or aromatic groups, and an apolar side, represented normally by chains of methyl groups —$CH_2$— from $C_6$ to $C_{10}$. Typical examples are di(2-ethylhexyl) phthalate (DEHP), di-isononyl phthalate (DINP), adipates of 2 ethyl hexyl alcohol phthalate. In any case, hundreds of other substances with plasticizing properties exist, but often they have niche applications because of lower ratio efficiency/cost.

Action of plasticizer like phthalates, referred to PVC is the following: polar carboxylic and aromatics groups interact with polar parts of polymer monomeric unit; apolar parts of plasticizer inserted between polymeric chain increase distance between them. The consequence is that the polymer obtains flexibility properties.

Phthalates, particularly DEHP, have been for long time the more used, because of good mechanical characteristics provided to the manufactures, poor tendency to exudation, even under high temperate and humidity conditions, and low costs compared to all the others. However, the classification of phthalates in the group of dangerous substances (R60-R61 cat. 2) and the insertion into the list of SVHC (substances of very high concern) have induced industry to use phthalates with longer hydrocarbon chain and thus with lower tendency to migrate out the product, as iso nonyl phthalate, but especially, to find new plasticizer with properties of no toxicity and environment safe.

WO 2012/018939 discloses methods for the manufacture of acetals and ketals with high selectivity for acetilization and ketalization over esterification or transesterification reactions. These methods yield the desired product in high yield and of high productivity, free of other side products or contaminants. The method is disclosed for the manufacture of a glycerol ketal of ehyl levulinate. However, the methods herein disclosed are rather complex and need as starting substance the ethyl levulinate, which is a quite complex molecule not particularly suitable as plasticizer.

WO 2010/036884 discloses compounds including polycarbonates, allylic monomers and polymerized or grafted products thereof, oxiranyl functional monomers and polymerized or grafted products thereof, and acrylate and methacrylate monomers and polymerized or grafted products thereof, derived from renewable biomass feedstocks. Said compounds are based on hydroxyl ketal carboxylate precursor, which precursor are known to be used as plasticizers for PCV. However, said compounds and precursors are rather complex to be synthetized and, thus, costly.

JP 10095748 discloses a glycerol-α-polyoxyalkylene glycerol monofatty acid ester to be used as surfactant.

RO 128511 discloses a pour point and limit filtrability temperature depressant additive for gas-oil and to a process for preparing the same. The additive consists of a hydrocarbonated solvent solution containing a copolymer which comprises vinyl acetate dialkylfumarate, the solvent consisting of alkanes, cycloalkanes, mononuclear aromatic or alkyl aromatic hydrocarbons or mixtures thereof, and C—C aliphatic acid ester with (2,2-dimethyl-[1,3]dioxolan-4-yl) methanol solketal.

WO 2009/010527 discloses a process for the preparation of acetals and ketals of glycerol or its monoesters and monoethers in order to reach high yields.

Plasticizers derived from vegetable oils (triglycerides), represent an interesting alternative. However, vegetable oils are not compatible with PVC, because of their low polarity. By treatment of epoxidation of hydrocarbon chains double bonds, oxygen is introduced into the molecule, and this increases compatibility with polar polymers. Therefore, more double bonds are present into the triglyceride, higher is solubility of epoxidized triglyceride.

Also, plasticizing property is increased by length of hydrocarbon chain. Longer is the chain, better is flexibility of product obtained. However, the length of hydrocarbon chain reduces solubility into the polymer network. This is the case of fatty acids, which have chains from $C_{12}$ to $C_{22}$: they could impart good flexibility but have poor solubility into PVC resin.

Epoxidation of double bonds of hydrocarbon chain of fatty acids allows to increase solubility into the polymer. The frequency of double bonds is an index of suitability of a fatty acid to be used as plasticizer. For instance, the glyceride of oleic acid, which derives from a $C_{18}$ fatty acid with one double bond, is less compatible respect to that of linolenic acid with two double bonds.

Soya oil is the more rich of insaturations among the most common vegetable oils. However, it is not possible to introduce more than 15% phr (that means 15 parts for 100 parts of polymer) of epoxidized soya oil into the PVC resin. In fact, over this concentration, oil begins to exude. For this reason, epoxidized oils may be used only as secondary plasticizers (moreover, epoxy function has also stabilizing action on PVC resin).

Epoxidized methyl ester of fatty acids from soya oil, known as biodiesel, has greater compatibility with PVC respect to other epoxidized oils, because it is a monoglyceride and thus has greater capacity to penetrate inside the tangle of polymeric chains. However, oils, which are triglycerides, with a molecular weight three times higher than mono-glycerides, have problems to introduce inside polymeric network. In addition, if from one side epoxidized methyl esters have greater solvency properties, on the other side, just by their low molecular weight and thready structure, migrate easier to the outside of polymer, giving it an oily appearance, and causing progressive worsening of product mechanical property (brittling).

In summary, to have a good vegetable origin plasticizer it is necessary to reach an optimum balance among: a) the flexibility of the molecule (property imparted by linear hydrocarbon chains), and b) compatibility with PVC (property imparted by ether bonds or oxirane bonds, while —OH groups are too much polar). Furthermore, the molecule must not migrate outside the polymer matrix (exudation). But good flexibility is in contrast to no exudation: in fact, for instance, epoxidated methyl esters of fatty acids give good flexibility but exude too much.

SUMMARY OF THE INVENTION

The technical problem solved by the present invention is, thus, to find new environmentally friendly and vegetable origin plasticizers, that give a good flexibility to product without causing exudation phenomena.

This problem is solved by vegetable origin plasticizers deriving from naturally occurring oils, having a molecular structure that allows their insertion among the polymeric chains of the final product to be plasticized in a stable and functional manner.

Therefore, a first object of the present invention is plasticizers of vegetable origin for polymers.

A second object is a method for producing plasticizers of present invention.

A third object is the use of said plasticizers for thermoplastic polymers and resins.

A further object of the invention is a process for plasticizing polymers or resins comprising the use of said plasticizers.

Additional features and the advantages of plasticizers of this invention will be more evident from the following description of some embodiments, given only for a purpose of exemplification and not in a limitative way.

DETAILED DESCRIPTION OF THE INVENTION

Following several experiments, it has been surprisingly found that esterifying fatty acid from naturally occurring vegetable oils with cyclic hydroxy acetals or hydroxy ketals and epoxidizing subsequently the double bonds contained into the hydrocarbon chains of the fatty acids, it is possible to obtain a product with plasticizing property and with high compatibility with for instance PVC.

In particular, it has been surprisingly discovered that by reaction of fatty acids from vegetable oils that contain double bonds into hydrocarbon chains with Glycerol Formal or Solketal, and subsequently epoxidizing the double bonds of the ester so obtained with usual methods, the resulting product provides a plasticizing property comparable with that of the petrochemical conventional plasticizers, without substantial exudation phenomena.

Glycerol Formal can be defined a cyclic hydroxy-acetal: this term is herein to be intended as indicating an acetal with an hydroxy function. It is composed by two isomers: 1,3 Dioxane-5-ol (isomer with rings of 6 atoms) and 1,3 Dioxolane-4-methanol (isomer with ring of 5 atoms). The structure of two isomers is the following:

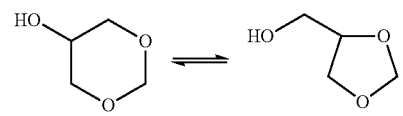 [SMILES: OC1COCOC1 ; OCC1COCO1]

Solketal has the following structural formula:

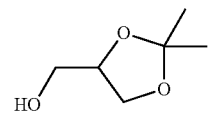

In particular, Glycerol Formal is obtained by reaction of Glycerol and Formaldehyde, and the isomers are produced with similar quantity (isomer with six atoms, more stable, is formed with a quantity lightly higher).

Then, because polarity of ether bonds Glycerol Formal esters are more compatible with PVC respect to esters of alcohols with hydrocarbon chain of comparable molecular weight. Consequently, esters of Glycerol Formal migrate to a less extent out of resin respect of esters with similar molecular weight but lower polarity.

For example methyl ester of epoxidized oleic acid has the following structure:

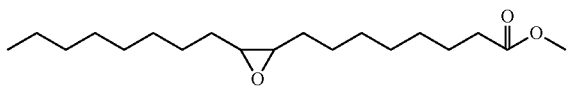 [SMILES: CCCCCCCCC1OC1CCCCCCCC(=O)OC]

While epoxidized ester of Glycerol Formal with oleic acid has the following structure:

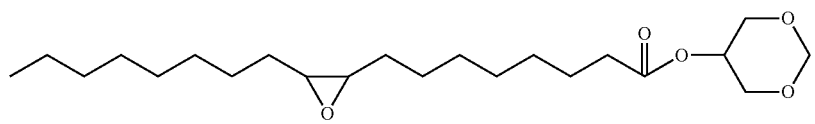 [SMILES: CCCCCCCCC1OC1CCCCCCCC(=O)OC1COCOC1]

Both esters have a polar carboxylic group, but while the first ester has one oxygen atom of the epoxy group, the second ester has two extra oxygen atoms of the acetal group. This could cause the epoxidized ester of Glycerol Formal to have stronger anchoring to the polymeric matrix.

Another important issue that has been found is that the acetals or ketals bonded to fatty acids are cyclic rings, with 5 or 6 atoms, that renders movements of the molecule more difficult through the tangle of polymer chains, consequently migration is reduced for steric hindrance. However, if the steric hindrance is excessive the plasticizing proprieties are loss and the final product is rigid and brittle. For example, an experiment has been carried out by esterifying adipic acid with glycerol formal in order to obtain a diester with a $C_6$ hydrocarbon chain and two cyclic rings with two oxygen atoms for each ring. The final product has been tested as plasticizer and the result was poor plasticizing properties. In this case the "anchoring" effect of acetals rings was too much excessive due to the presence of two cyclic rings per molecule of plasticizer, while the "flexibility" effect of chain of the fatty acids was too much poor (length of hydrocarbon chain only $C_4$). Therefore, it has also been found that is also very important to balance from one hand the presence of cyclic acetals or ketal and from the other hand the number of cyclic acetals and ketals present in the plasticizer, and also the length of the fatty acid chain, which chain is known to be apolar.

In addition, it is to be noticed that if the unsaturated ester according to the present invention is not epoxidized, it cannot be a good plasticizer: in fact it has been observed too much exudation phenomena because the content of oxygen in the molecule is too low. However, if the esters of present invention of saturated fatty acids are mixed with esters of insaturated fatty acids the exudation is reduced. Thus, esters of fatty acids from palm oil, with low insaturated content, are less valid plasticizers respect to esters of fatty acids from soybean oil, with high insaturated content.

Therefore, the disadvantage of the prior art concerning the use of vegetable oil, caused by compatibility with polymer (epoxidized soya oil) and migration (methyl esters of epoxidized soya oil), are overcome by the present invention.

With respect to plasticizers based on conventional epoxidized soya oil, which cannot be used with a concentration higher than 15% phr due to the exudation phenomena, plasticizers of the present invention can be used without compatibility or exudation problems up to 50% phr and over.

Moreover, at the same manner of known epoxidized oils, the compounds of the present invention can act as thermal co-stabilizers, but because their higher content, the stabilizing activity is increased proportionally.

Esters of epoxidized fatty acids and Glycerol Formal have the feature of being almost completely of vegetable origin. In particular, the carboxylic part of ester can be obtained through transesterification of vegetable oils, transesterification of methyl esters of vegetable oils, or by splitting of vegetable oils (fatty acids), and Glycerol Formal can be obtained from Glycerol (a by-product of biodiesel production) by reaction of Glycerol with formaldehyde. Since in the esters according to the present invention the not vegetable-origin portion derives only by the formaldehyde used for modify Glycerol, it has been calculated that about 96% of this ester is of vegetable origin. Similar considerations are valid for epoxidized esters of Solketal (2,2 Dimethyl-1,3 Dixolan 4-yl) methanol.

Preferably, on the basis of various experiments, it has been found that any cyclic hydroxy-acetal, or hydroxy-ketal esterified with epoxidized carboxylic acids with hydrocarbon chain from $C_{12}$ to $C_{22}$ has plasticizing properties. With reference to $C_{12}$-$C_{22}$ fatty acids, specific experiments have been carried out with vegetable oils comprising different amounts of stearic, palmitic, oleic, linoleic, linolenic fatty acids. In particular, the vegetable oils have been selected from the table reported in the attached FIG. 1, wherein for each vegetable oil has been specified the kind and amount of the fatty acids.

Synthesis of Epoxidized Natural Fatty Acids Esters of Hydroxy Acetals and Hydroxy Ketals Epoxy esters between carboxylic acids and hydroxy acetals or ketals of this invention can be obtained by direct esterification of fatty acid, transesterification of methyl ester or transesterification of vegetable oil. Transesterification of oils gives the esters of the fatty acids which are typical for that triglyceride.

Direct esterification with hydroxyl acetals or hydroxy ketals could be complicated because water coming from reaction decomposes ethers bonds with consequent release of the corresponding aldehyde or ketone. However, managing the reaction in order to evaporate immediately water as soon as is formed, decomposition of hydroxyacetals is insignificant.

Therefore, for esterifying, the better solution is to operate with vacuum, however not till to have evaporation of hydroxy-acetal. In particular, carrying out the esterification in the presence of an acid catalist at a temperature between 60° C. and 200° C., preferably between 80° C. and 120° C., for a time ranging between 8 and 10 hours, it is sufficient keeping a vacuum between 0 and 100 mbar, preferably from 0 mbar and 50 mbar, depending on the reaction temperature selected. The hydroxy acetal aliquot which evaporates together with water is subsequently recovered by distillation. When Glycerol Formal is used, this recovery is simple because since it boils at 192°-195° C., while the water boils at 100° C., such a difference renders easy their separation. The distillation can also be carried out during the reaction, causing the vapors to flow towards the bottom of a plate or fill column provided with a condensation system for the head vapors of the column positioned upon the reactor: the vapors condensing into the column, represented by Glycerol Formal, fall down into the reactor, while the head vapors represented by water are condensed and collected separately.

Other methods useful to eliminate water are the introduction into the reactor of a solvent that is able to do azeotropes with water or blowing with an inert gas as nitrogen. It is also possible to combine said methods with the one above described.

Transesterification of the methyl ester is carried out heating under stirring at a cyclic acetal or ketal and a methyl ester of a vegetable oil in the presence of a base or an acid. The reaction is carried out for 6-10 hours and the methanol produced is eliminated by nitrogen blowing and under vacuum. At the end of the reaction, the mixture is neutralized. Subsequently, excess of Glycerol Formal not reacted is evaporated, heating the mixture under vacuum. Finally, Glycerol Formal is filtered in order to neutralize salts eventually produced during neutralization.

Transesterification of vegetal oil is carried out heating under stirring a cyclic acetal or ketal and a vegetable oil in the presence of a basic or acid catalyst or a transition metal (like 2-ethyl hexyl titanate) at a temperature comprised between 70°-120° C. for 6-12 hours, subsequently cooling the mixture at a temperature of about 60° C. and neutralizing the catalyst. Afterwards, the mixture is separated into an oil phase and a glycerol phase by means of decantation and, then, the oil phase is washed with water to eliminate Glycerol Formal and glycerol. Conversely, the glycerol phase is distilled in order to separate Glycerol Formal and glycerol. In this manner, Glycerol Formal can be advantageously recovered.

Once the ester has been synthetized, the epoxidation is carried out with conventional methods used for epoxidising vegetable oils or their esters. Said methods comprises keeping a mixture of fatty acids or fatty acid ester, ester or vegetable oil with formic acid and hydrogen peroxide at a temperature of 25-60° C. for 8-12 hours.

Production of a Polymer or Resin Plasticized

Once the plasticizer according to the present invention is obtained according to the above method, in order to produce a plasticized polymer or resin, a conventional process can be carried out. In particular, the process comprises a step of mixing for 100 phr of a liquid polymer or resin 30-70 phr of a plasticizer according to the invention.

Therefore, a further object of the present invention is a composition comprising a thermoplastic polymer and an ester and/or an epoxide ester as above.

In the following examples are reported some synthesis of plasticizers according to the present invention and a comparison example between a known plasticizer and a plasticizer according to the present invention.

The preferred vegetable oil is soybean oil because has an high content of double bonds and is the most common vegetable oil. Typical fatty acids composition of soybean is: poly-unsaturates, linolenic acid (C-18:3), 7-10% and linoleic acid (C-18:2), 48-52%; mono-unsaturate, oleic acid (C-18:1), 19-30%; saturated fatty acids, stearic acid, (C-18: 0), 2-5% and palmitic acid, (C-16:0), 7-12%.

Example 1

Esterification of Soybean Fatty Acid with Glycerol Formal

A flask of 2 liters capacity equipped with stirrer, thermometer, manometer and a condenser for distillates, is charged with 500 grams of Glycerol Formal and 12 grams of p-toluen sulfonic acid. The mixture is stirred and heated to 50° C. and then are added 1000 grams of soya bean fatty acid. Subsequently, the mixture is heated to 90° C. and leaved at this temperature for 8-10 hours. During this time, elimination of water of reaction from mixture is facilitated by nitrogen blowing into the mixture and keeping pressure into the flask at 10-30 mbar with a vacuum pump.

Progress of the reaction is monitored by acidity determination on samples extracted during the reaction. When acidity reaches values lower than 5 mgr KOH/gr, the mixture is cooled to 50° C. and a sufficient quantity of 50% caustic soda solution is added to neutralize acidity. Then the mixture is heated to 130° C. under a vacuum into the flask of 20 mbar, in order to evaporate the excess of Glycerol Formal not reacted. Finally, the ester of Glycerol Formal is filtered in order to neutralize salts produced during neutralization.

Epoxidation of the Ester

A flask of 2 liters capacity equipped with stirrer and thermometer, placed into a bath in order to control temperature of reaction mixture, is charged with 700 grams of ester previously obtained and 80 grams of 85% wt Formic acid. Then, the mixture is stirred and heated to 45° C. and 200 grams of 50% Hydrogen Peroxide are slowly added during a period of 60 minutes, keeping reaction temperature at 45° C. by cooling the bath. The mixture is maintained at 45° C. for additional 6 hours. During this time the progress of reaction is followed by determination of oxyrane/oxygen content in samples of reaction mixture withdrawn off. Finally the mixture is placed into a separator funnel and is herein maintained at 40-50° C. for 1 hour in order to obtain an oil phase (upper layer) and an aqueous phase (lower layer) in the reactor. Thereafter, the two phases are separated. The aqueous phase is drained off and the oil phase is washed two times with 200 ml of 10% sodium chloride solution each time. An epoxidized ester with oxirane number of 4-4,5 and iodine number of 4-10 was obtained.

Example 2

Transesterification Soybean Oil with Glycerol Formal

A flask of 2 liters capacity equipped with stirrer, thermometer, manometer and a condenser for distillates, is charged with 850 grams of Glycerol Formal and 50 grams of 25% sodium methylate. The mixture is stirred and heated to 50° C. and subsequently 1000 grams of soya oil are added. Therefore, the mixture is heated to 90° C. and leaved at this temperature.

After 8 hours the mixture is cooled to 60° C. Then a sufficient quantity of diluted sulfuric acid solution is added to neutralize basicity. Later, the mixture is transferred to a separator funnel where stays in decantation for 2 hours. During decantation the mixture is cooled to 50° C. Then is separated in two phases. Most of Glycerol generated during reaction is collected in the heavy layer. The oily light layer is washed with water in order to eliminate Glycerol and Glycerol Formal which are dissolved, while heavy layer is distillated: at the top of column the Glycerol Formal is collected and at the bottom Glycerol is collected.

Epoxidation of the Ester

The method is the same as described in Example 1.

Example 3

Transesterification Methyl Soyate with Glycerol Formal

A flask of 2 liters capacity equipped with stirrer, thermometer, manometer and a condenser for distillates, is charged with 800 grams of Glycerol Formal and 50 grams of a 25% solution of sodium methylate. The mixture is heated to 50° C. and then 1000 grams of methyl ester fatty acid from soybean oil are added. Subsequently, the mixture is heated to 190° C. and leaved at this temperature for 4 hours. During this time, elimination of methanol obtained from reaction is carried out by nitrogen blowing into the mixture and keeping pressure into the flask at 10-30 mbar with a vacuum pump.

Progress of the reaction is monitored by GAS chromatography of samples taken during reaction. When transesterification is finished a sufficient quantity of diluted sulfuric acid is added to neutralize acidity. Then, the mixture is heated to 130° C. under 20 mbar vacuum into the flask, in order to evaporate the excess of Glycerol Formal not reacted. Finally, the ester of Glycerol Formal is filtered in order to separate salts produced during neutralization.

Epoxidation of the Ester

The method is the same as described in example 1.

Example 4

A comparison of plasticizing properties of a plasticizer of present invention with a typical palsticizer of petrochemical origin as di isononyl phtalate was done through conventional tests.

A formulation for flexible PVC with the composition of the Table 1 was prepared.

TABLE 1

| Substance | Amount (phr) |
| --- | --- |
| PVC resin K | 100 |
| Plasticizer | 62 |
| Secondary plasticizer (ESBO) | 3 |
| Stabilizer (Zn/Ca stearate) | 0.95 |
| Lubricant (Stearic acid) | 0.25 |

As Plasticizer of present invention, epoxidized soybean ester of Glycerol Formal, produced in one of the methods described above, was selected. For comparison, di (iso nonyl) phatalate (DINP), one of the most common plasticizers, was selected.

Components of the above formulation of Table 1 where mixed together in a turbomix at temperature of 70-80° C. for 30 min. Then the mixture was processed in a laboratory calendar with rollers heated at 160° C. in order to produce sheets of plasticized PVC. Afterwards, to obtain constant thickness of 0.5 mm, the sheets were rolled and pressed in molds (200° C., 100 bar). Finally the sheets were cut into test bodies (15 mm×15 mm) that were used to determine their performance properties. Results are reported in the following Table 2 wherein the tests have been carried out according to the standards specified.

TABLE 2

| Property | PCV + DINP | PVC + Plasticizer of the invention |
| --- | --- | --- |
| Shore A hardness (ISO 868) | 70 | 67 |
| Mass loss (ISO 176) % Method A | 0.28 | 0.37 |
| Breaking force (EN ISO 527-2) N/mm$^2$ | 15 | 16 |
| Deformation (EN ISO 5272-2) % | 390 | 460 |

Data of Table 2 show that plasticizers of present invention can be used as primary plasticizers. Performances are similar to that one of most appreciated petrochemical plasticizers.

The invention claimed is:

1. Esters of carboxylic acids with cyclic acetals or ketals, wherein the double bonds of the hydrocarbon chain of the carboxylic acids are epoxidized.

2. Esters according to claim 1, wherein the carboxylic acids are selected from fatty acids having a hydrocarbon chain comprised between C12 and C22, the acetal is glycerol formal and the ketal is solketal.

3. Esters according to claim 2, wherein the carboxylic acids are selected from oleic, linoleic, and linolenic fatty acids of vegetable oil selected from soybean, sunflower, rapeseed, linseed, palm, canola and a mixture thereof.

4. Process for producing the esters according to claim 1 by direct esterification, comprising the steps of:
heating under stirring a cyclic acetal or ketal and a fatty acid in the presence of acid catalyst;
bringing the mixture so obtained at reaction temperature between 60° C. and 200° C. and, at the same time, eliminating water that forms during the esterification reaction between the cyclic acetal or ketal and carboxylic acid at a pressure value between 0 and 300 mbar;
cooling and neutralizing the mixture with a base at the end of the esterification reaction;
eventually heating under vacuum the mixture for evaporating the cyclic acetal or ketal in excess that does not react, and recovering the ester;
epoxidizing the double bonds of the ester recovered.

5. Process for producing the esters according to claim 1 by transesterification of vegetable oils comprising the steps of:
heating under stirring a cyclic acetal or ketal and a vegetable oil in the presence of a basic catalyst at a temperature comprised between 70°–120° C. for 6-12 hours;
cooling and neutralizing the catalyst with acid;
separating the oil phase from the glycerol phase with decantation;
washing the oil phase with water;
epoxidizing the ester contained in said oil phase.

6. Composition comprising a thermoplastic polymer and an ester according to claim 1.

7. Process for plasticizing a polymer or resin comprising a step of mixing for 100 phr of a liquid polymer or resin, 30-70 phr of an ester according to claim 1.

* * * * *